(12) United States Patent
Nakamura et al.

(10) Patent No.: US 9,850,189 B2
(45) Date of Patent: Dec. 26, 2017

(54) METHOD FOR PRODUCING TRIFLUOROETHYLENE

(71) Applicant: Asahi Glass Company, Limited, Chiyoda-ku (JP)

(72) Inventors: Masahiko Nakamura, Chiyoda-ku (JP); Hidekazu Okamoto, Chiyoda-ku (JP)

(73) Assignee: Asahi Glass Company, Limited, Chiyoda-ku (JP)

( * ) Notice: Subject to any disclaimer, the term of this patent is extended or adjusted under 35 U.S.C. 154(b) by 0 days.

(21) Appl. No.: 15/273,140

(22) Filed: Sep. 22, 2016

(65) Prior Publication Data
US 2017/0008823 A1    Jan. 12, 2017

Related U.S. Application Data

(63) Continuation of application No. PCT/JP2015/059140, filed on Mar. 25, 2015.

(30) Foreign Application Priority Data

Mar. 27, 2014 (JP) ................. 2014-066058

(51) Int. Cl.
C07C 17/25 (2006.01)
C07C 17/38 (2006.01)
B01J 23/26 (2006.01)

(52) U.S. Cl.
CPC ............ *C07C 17/25* (2013.01); *B01J 23/26* (2013.01); *C07C 17/38* (2013.01)

(58) Field of Classification Search
CPC .................................................. C07C 17/25
See application file for complete search history.

(56) References Cited

U.S. PATENT DOCUMENTS

| 5,856,593 A | 1/1999 | Powell et al. |
| 2004/0070132 A1 | 4/2004 | Varzino et al. |
| 2010/0185029 A1 | 7/2010 | Eisheikh et al. |
| 2010/0191024 A1 | 7/2010 | Uenveren et al. |
| 2011/0201852 A1 | 8/2011 | Pigamo et al. |

FOREIGN PATENT DOCUMENTS

| JP | 10-505337 | 5/1998 |
| JP | 2010-531897 | 9/2010 |
| JP | 2010-533151 | 10/2010 |
| JP | 2012-502084 | 1/2012 |

OTHER PUBLICATIONS

International Search Report dated Jun. 16, 2015 in PCT/JP2015/059140, filed on Mar. 25, 2015.

*Primary Examiner* — Medhanit W Bahta
(74) *Attorney, Agent, or Firm* — Oblon, McClelland, Maier & Neustadt, L.L.P.

(57) ABSTRACT

To provide a production process with high degree of conversion of HFC-134a and selectivity for HFO-1123, with a high productivity of HFO-1123 and with a small load in process of purification and recovery.
A process for producing HFO-1123, which comprises bringing a material gas having a proportion of HFC-134a based on the total amount of a diluent gas and HFC-134a of from 50 to 100 mol % into contact with a dehydrofluorination catalyst to convert part of HFC-134a into HFO-1123, then removing hydrogen fluoride in a reaction product gas, and then bringing the reaction product gas from which hydrogen fluoride has been removed into contact with a dehydrofluorination catalyst to convert at least part of unreacted HFC-134a into HFO-1123.

13 Claims, 1 Drawing Sheet

METHOD FOR PRODUCING TRIFLUOROETHYLENE

TECHNICAL FIELD

The present invention relates to a process for producing trifluoroethylene, more particularly, a process for efficiently producing trifluoroethylene from 1,1,1,2-tetrafluoroethane.

BACKGROUND ART

Trifluoroethylene (HFO-1123), which has a low global warming potential (GWP), is greatly expected in recent years as a new refrigerant which may replace difluoromethane (HFC-32) and 1,1,1,2,2-pentafluoroethane (HFC-125) which are greenhouse gases.

In this specification, abbreviated names (e.g. refrigerant numbers) of halogenated hydrocarbon compounds are described in brackets after the compound names. As the case requires, the abbreviated names are employed instead of the compound names.

Heretofore, as a process for producing HFO-1123, a process of using as a material 1,1,1,2-tetrafluoroethane (HFC-134a) which is a relatively inexpensive material has been known. For example, Patent Documents 1 and 2 disclose a process of subjecting HFC-134a to dehydrofluorination using a metal fluoride or a metal oxide as a catalyst to obtain HFO-1123.

However, by the production process disclosed in Patent Documents 1 and 2, since the reaction is conducted in a state where a large amount of nitrogen is mixed with HFC-134a so as to increase the degree of conversion of HFC-134a, nitrogen is contained in a large amount in the formed gas obtained after completion of the reaction (for example, outlet gas from the reactor). Accordingly, the content of the desired HFO-1123 is low in the formed gas, and the productivity is not satisfactory high. Further, since nitrogen is contained in a large amount in the formed gas, a load in the subsequent process such as purification of HFO-1123 and recovery of HFC-134a and nitrogen tends to be heavy, utility costs such as electricity are high, and large facilities are required for the purification and recovery.

Accordingly, to produce HFO-1123 useful as a new refrigerant which replaces greenhouse gases using HFC-134a which is an inexpensive material, an efficient production process with an improved degree of conversion of HFC-134a and with high productivity has been desired.

PRIOR ART DOCUMENTS

Patent Documents

Patent Document 1: JP-A-2010-533151
Patent Document 2: JP-A-10-505337

Disclosure of Invention

Technical Problem

Under these circumstances, it is an object of the present invention to provide a process for producing HFO-1123 by using HFC-134a which is an inexpensive material, with improved degree of conversion of HFC-134a and selectivity for HFO-1123 and with high productivity.

Solution to Problem

The process for producing HFO-1123 of the present invention comprises bringing a HFC-134a gas or a HFC-134a gas diluted with a diluent gas (provided that the proportion of HFC-134a based on the total amount of the diluent gas and HFC-134a is at least 50 mol %) into contact with a first dehydrofluorination catalyst to convert part of HFC-134a into HFO-1123, then removing hydrogen fluoride from the reaction product gas obtained by the above reaction, and then bringing the reaction product gas from which hydrogen fluoride has been removed into contact with a second dehydrofluorination catalyst to convert at least part of HFC-134a into HFO-1123.

Advantageous Effects of Invention

According to the production process of the present invention, when HFO-1123 is produced from HFC-134a which is a relatively inexpensive material, the degree of conversion of HFC-134a and the selectivity for HFO-1123 are sufficiently high. Further, the content of HFO-1123 in the reaction product gas obtained by the reaction is high, and the productivity of HFO-1123 is high.

DESCRIPTION OF EMBODIMENTS

Figure 1:
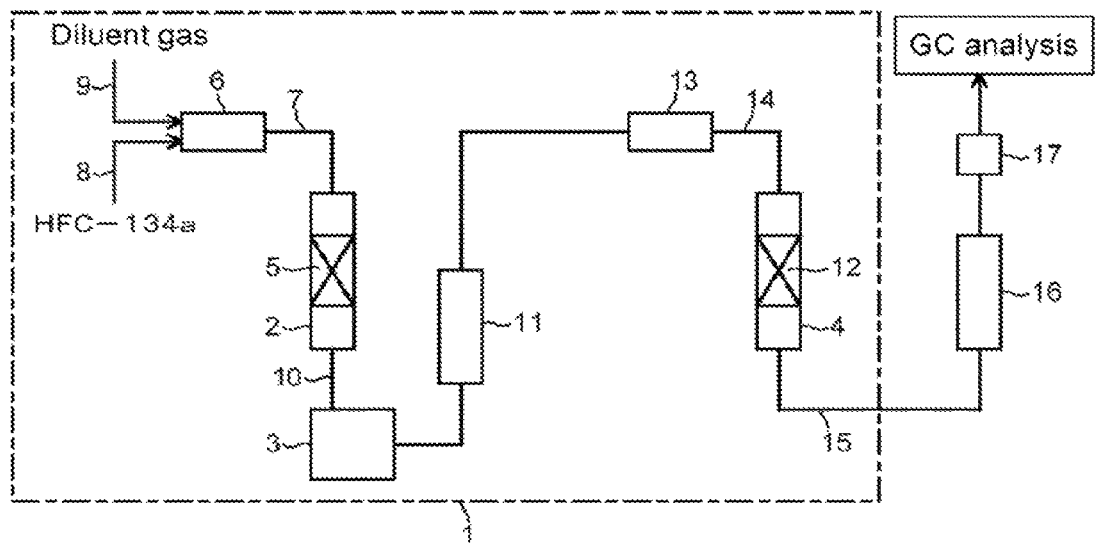
FIG. 1 is a diagram illustrating an example of a reaction apparatus used for the production process of the present invention.

In this specification, hereinafter, "the HFC-134a gas or the HFC-134a gas diluted with a diluent gas (provided that the proportion of HFC-134a based on the total amount of the diluent gas and HFC-134a is at least 50 mol %)" will be referred to as a material gas.

Further, "the first dehydrofluorination catalyst" will be referred to as "catalyst (1)", and "the second dehydrofluorination catalyst" will be referred to as "catalyst (2)".

Further, the step of bringing the material gas into contact with the catalyst (1) to conduct a reaction of converting part of HFC-134a into HFO-1123 will be referred to as "step (I)", the step of removing hydrogen fluoride from the reaction product gas obtained by the reaction in the step (I) will be referred to as "step (II)", and the step of bringing the reaction product gas from which hydrogen fluoride has been removed into contact with the catalyst (2) to conduct a reaction of converting at least part of unreacted HFC-134a into HFO-1123 will be referred to as "step (III)".

In the present invention, formation of HFO-1123 by dehydrofluorination of HFC-134a by the contact with each of the catalyst (1) and the catalyst (2) may be represented by the following reaction formula (1):

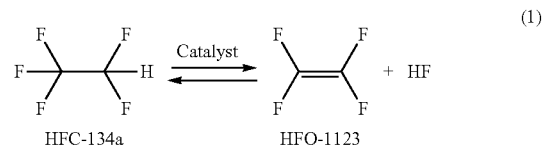

(1)

By bringing the HFC-134a gas into contact with the catalyst (1) or (2), dehydrofluorination occurs in which one of fluorine atoms bonded to a carbon atom to which three fluorine atoms are bonded between the two carbon atoms of HFC-134a, and one of hydrogen atoms bonded to the other carbon atom, leave simultaneously. And, by such dehydrofluorination of HFC-134a, HFO-1123 and hydrogen fluoride simultaneously form.

Such dehydrofluorination of HFC-134a is an equilibrium reaction and reversively proceeds, and by removing formed hydrogen fluoride from the reaction system, the degree of conversion of HFC-134a in dehydrofluorination may be increased.

Accordingly, in the production process of the present invention, by converting part of HFC-134a in the material gas into HFO-1123 and removing hydrogen fluoride in the obtained reaction product gas, the reversible reaction of the reaction formula (1) proceeds to the desired product HFO-1123 side in a degree corresponding to the reduction of hydrogen fluoride, when the reaction product gas is brought into contact with the catalyst (2) in the subsequent step, and accordingly the degree of conversion of HFC-134a and the selectivity for HFO-1123 can be sufficiently high.

Further, in a case where a material gas containing a diluent gas is used in the production process of the present invention, the content of the diluent gas in the gas obtained after completion of the step (III) is low, and the content of HFO-1123 is relatively high. Accordingly, the load in the subsequent process of purification of HFO-1123 and recovery of HFC-134a and the diluent gas can be reduced, and the production process is excellent in the productivity.

The production process of the present invention may be a totally continuous production process in which the steps (I) to (III) are continuously carried out, or may be a partially continuous production process in which one or two among the three steps (I), (II) and (III) are carried out by the batch and the other step is continuously carried out, so long as the process comprises the steps (I), (II) and (III) in this order. Otherwise, it may be a total batch production process in which all the three steps are conducted by the batch.

In a case where the step (I) is a continuous step, supply of the material gas and the catalyst (1) to the site of contact (for example, a heated reactor) may be such that both the material gas and the catalyst (1) are supplied continuously, or only one of the material gas and the catalyst (1) is continuously supplied, and the other is supplied by the batch. With a view to shortening the maintenance time to increase the productivity, it is preferred to supply the catalyst (1) to a reactor by the batch and then to supply the material gas continuously to the reactor.

In the same manner as the above step (I), the step (II) may be a continuous step or may be a batch step. However, with a view to shortening the maintenance time to increase the productivity, the step (II) is preferably a continuous step.

Further, the step (III) may also be a continuous step or may be a batch step.

In a case where the step (III) is a continuous step, supply of the reaction product gas after removal of hydrogen fluoride and the catalyst (2) to the site of contact (for example, a heated reactor) may be such that both are continuously supplied, or only one of them is supplied continuously and the other is supplied by the batch. With a view to shortening the maintenance time to increase the productivity, it is preferred to supply the catalyst (2) to a reactor by the batch and then to supply the reaction product gas after removal of hydrogen fluoride continuously to the reactor.

Now, the steps (I), (II) and (III) will be described in further detail.

<Step (I)>

In the step (I), the material gas is brought into contact with the catalyst (1) to convert HFC-134a in the material gas into HFO-1123.

(Material Gas)

The material gas may be a HFC-134a gas or a HFC-134a gas diluted with a diluent gas. In the case of the HFC-134a gas diluted with a diluent gas, the proportion of HFC-134a based on the total amount of the diluent gas and HFC-134a is at least 50 mol %.

The proportion of HFC-134a based on the total amount of HFC-134a and the diluent gas in the material gas is at least 50 mol % with a view to achieving sufficiently high degree of conversion of HFC-134a and selectivity for HFO-1123 and to increasing the content of HFO-1123 in the reaction product gas obtained in the step (I). The proportion of HFC-134a is preferably at least 70 mol %, more preferably from 70 to 100 mol %, further preferably from 90 to 100 mol %, particularly preferably from 95 to 100 mol %, most preferably from 99 to 100 mol %.

The diluent gas is a compound which is not consumed by dehydrofluorination and removal of hydrogen fluoride in the present invention, and may, for example, be nitrogen, argon, helium, trifluoromethane (HFC-23), HFC-32 or tetrafluoromethane (HFC-14). The diluent gas is particularly preferably nitrogen.

The material gas may contain a compound other than HFC-134a and the diluent gas, which is less likely to impair dehydrofluorination. Such a compound may be a compound which can be considered as a diluent gas, or may be a compound which is to be removed together with hydrogen fluoride at the time of removal of hydrogen fluoride (for example, an acidic substance such as hydrogen chloride). For example, 1,1,2,2-tetrafluoroethane (HFC-134), 1,1,1-trifluoroethane (HFC-143a), HFC-125, 2,2,2,3-tetrafluoropropene (HFO-1234yf), oxygen, chlorine, hydrogen chloride and the like, which are impurities derived from production of HFC-134a and which are contained in the material HFC-134a, may be mentioned.

The amount of the compound other than HFC-134a and the diluent gas (provided that the compound which can be considered as a diluent gas is considered as the diluent gas) in the material gas is preferably from 0 to 10 mol %, more preferably from 0 to 5 mol %, most preferably from 0 to 1 mol %, with a view to suppressing a side reaction of deterioration of the catalyst and with a view to suppressing unnecessary by-products and reducing the load in the subsequent purification step.

Further, although the material gas may contain the desired product HFO-1123, HFO-1123 contained in the material gas may cause a reverse reaction of the reaction to form HFO-1123 in the equilibrium reaction represented by the reaction formula (1). From such a viewpoint, the proportion of HFO-1123 in the material gas is preferably from 0 to 20 mol %, more preferably from 0 to 10 mol %, most preferably from 0 to 5 mol %.

Further, the material gas may contain hydrogen fluoride, and from the same reason as above, its amount is preferably at most 1 mol %.

(Catalyst (1))

The catalyst (1) used in the step (I) has catalytic action on dehydrofluorination of HFC-134a. The catalyst (1) may, for example, be an elemental metal, a metal oxide or a metal halide. Among them, preferred is a metal oxide or a metal halide, with which HFC-134a can be efficiently converted into HFO-1123. The catalyst (1) may be used alone or in combination of two or more.

The metal constituting the elemental metal, the metal oxide or the metal halide may be a transition metal element, a group 12 metal element or a group 13 metal element. Among them, preferred is a group 6 metal element, a group 8 metal element, a group 10 metal element, a group 12 metal element or a group 13 metal element, more preferred is chromium, iron, zinc or aluminum.

The elemental metal catalyst may consist of one of the above metals or may be an alloy of two or more metals.

The metal oxide catalyst may be an oxide of one of the above metals or may be a composite oxide of two or more metals.

The metal halide may be a halide of one of the above metals or may be a composite halide of two or more metals.

The catalyst (1) may, for example, be specifically cobalt, nickel, palladium, chromium oxide (chromia), aluminum oxide (alumina), zinc oxide, iron fluoride, aluminum fluoride, aluminum chloride, chromium fluoride, chromium chloride or zirconia. Among them, preferred is alumina, aluminum trifluoride or chromia with which HFC-134a can be efficiently converted into HFO-1123.

The specific surface area of the catalyst (1) measured by the BET method (hereinafter referred to as the BET specific surface area) is preferably from 50 to 400 m$^2$/g. When the BET specific surface area of the catalyst (1) is within the above range, HFC-134a will react at a high reaction rate and the reaction efficiency is thereby high, and in addition, the density of particles of the catalyst (1) is not too low, whereby the catalyst (1) is less likely to fly and its handling efficiency is favorable. The BET specific surface area of the catalyst (1) is more preferably from 200 to 400 m$^2$/g.

The catalyst (1) may be supported on a carrier. The carrier here is to improve the reaction efficiency of the catalyst (1) and the material gas by supporting the catalyst (1), and the carrier itself may have catalytic activity. The carrier may, for example, be an alumina carrier, a zirconia carrier, a silica carrier, a silica-alumina carrier, a carbon carrier represented by activated carbon, a barium sulfate carrier or a calcium carbonate carrier. The activated carbon may, for example, be activated carbon prepared from a material such as wood, charcoal, fruit shell, coconut shell, peat, lignite or coal.

The catalyst (1) is preferably preliminarily subjected to an activation treatment with a view to improving the degree of conversion. The method of the activation treatment may be a method of bringing the catalyst (1) into contact with an activating agent with heating or without heating. The activating agent may, for example, be oxygen, hydrogen fluoride, hydrogen chloride or a fluorinated carbon compound, and among them, a fluorinated carbon compound is preferred. The fluorinated carbon compound may, for example, be HFC-134a, HFO-1123, trichlorofluoromethane (HFC-11), dichlorofluoromethane (HFC-21), chlorodifluoromethane (HFC-22) or tetrafluoroethylene (FO-14).

Further, with a view to suppressing a side reaction and improving the durability of the catalyst (1), an inert gas such as nitrogen, argon or helium may be used to dilute the activating agent.

The catalyst (1) may be subjected to a reactivation treatment in addition to such an activation treatment before the reaction. That is, when the activity of the catalyst (1) in the conversion reaction is decreased, and the degree of conversion of the material component HFC-134a and the selectivity for the desired product HFO-1123 are decreased, the catalyst (1) is preferably subjected to an activation treatment again. By the reactivation treatment, the activity of the catalyst (1) is regenerated to recycle the catalyst (1).

The reactivation treatment method may be a method of bringing the catalyst (1) into contact with the activating agent with heating or without heating, in the same manner as the activation treatment before use.

(Contact of Material Gas and Catalyst (1))

When the material gas and the catalyst (1) are brought into contact with each other, the catalyst (1) in a solid state (solid phase) may be brought into contact with the material gas, or the catalyst (1) in a state as dispersed in a liquid medium in which the catalyst (1) can be dispersed (liquid phase) may be brought into contact with the material gas. The liquid medium in which the catalyst (1) is dispersed may, for example, be water, an alcohol such as methanol or ethanol, a chlorine-based solvent such as carbon tetrachloride or N,N-dimethylformamide, N,N-dimethylacetamide, dimethylsulfoxide, tetraethylene glycol dimethyl ether, triethylene glycol dimethyl ether, diethylene glycol dimethyl ether or propylene glycol monomethyl ether monoacetate. In a case where the material gas is brought into contact with the catalyst (1) dispersed in a liquid medium, the pressure of the material gas is too high and high temperature reaction tends to be difficult, and accordingly it is preferred that the catalyst (1) in a solid phase and the material gas are brought into contact with each other.

Now, the step (I) will be described with reference to an embodiment in which the material gas continuously supplied to the reactor is brought into contact with the catalyst (1) in a solid phase charged to the reactor by the batch, however, the step (I) in the production process of the present invention is not limited to such an embodiment.

In the embodiment in which the material gas is continuously brought into contact and reacted with the catalyst (1) in the solid phase, the content (mol %) of HFC-134a in the material gas can be controlled by controlling the flow rate of each component in the material gas per unit time.

(Reactor and Reaction Conditions)

The reactor in which the material gas and the catalyst (1) are brought into contact and reacted with each other (hereinafter sometimes referred to as a first reactor) in the step (I) is not particularly limited in terms of the shape and the structure so long as the reactor can withstand the temperature and the pressure described hereinafter. The reactor may, for example, be a cylindrical vertical reactor. As the material of the first reactor, glass, iron, nickel, or an alloy containing iron or nickel as the main component may, for example, be mentioned. The first reactor may have a heating means such as an electric heater to heat the interior of the reactor.

The catalyst (1) charged into the first reactor and is in a solid phase may be accommodated in the form of either a fixed bed or a fluidized bed. Further, in the case of a fixed bed, it may be either a horizontal fixed bed or a vertical fixed bed, however, in a case where the material gas is a gas mixture consisting of several components, preferred is a vertical fixed bed, whereby concentration distribution of the respective components due to a difference in the specific gravity tends to be prevented.

The material gas may be introduced to the first reactor at room temperature as it is, however, it is preferably heated (preheated) and then introduced to the first reactor, so as to increase the reactivity in the reactor. In a case where it is preheated, the material gas is preferably heated to a temperature of from 80 to 150° C. and then supplied to the first reactor.

The material gas introduced to the first reactor is brought into contact with the catalyst (1) in a solid phase in the first reactor. The temperature in the first reactor is preferably from 50 to 500° C., more preferably from 200 to 500° C., particularly preferably from 300 to 450° C., by the contact temperature, with a view to improving the reactivity and the life of the catalyst. The pressure in the first reactor is preferably from 0 to 2 MPa by the gauge pressure. The contact time of the material gas and the catalyst (1) in the first reactor is preferably from 0.1 to 500 seconds, more preferably from 0.5 to 50 seconds, particularly preferably from 5 to 30 seconds.

(Reaction Product Gas Obtained in Step (I))

In the step (I), as the outlet gas from the first reactor, a reaction product gas containing HFO-1123 and unreacted HFC-134a (hereinafter referred to as reaction product gas (1)) is obtained. The reaction product gas (1) may contain, in addition to the desired HFO-1123, unreacted HFC-134a, the diluent gas contained in the material gas and other compounds formed in the step (I) (hereinafter referred to as by-product compounds). By-product compounds contained in the reaction product gas (1) may, for example, be hydrogen fluoride, E/Z-1,2-difluoroethylene (E/Z-HFO-1132), 1,1-difluoroethylene (HFO-1132a), 1,1,2-trifluoroethane (HFC-143), methane, ethane, ethylene, propane, propylene, n-butane, isobutane, 1-n-butene, 2-n-butene, isobutene, fluoroethylene (HFO-1141), 3,3-difluoropropene (HFO-1252zf), 3,3,3-trifluoropropene (HFO-1243zf), 2,3,3,3-tetrafluoropropene (HFO-1234yf), E/Z-1,3,3,3-tetrafluoropropene (E/Z-HFO-1234ze), hexafluoropropylene (FO-1216), HFC-125, HFC-134, 1,1,1-trifluoroethane (HFC-143a), 1,1,1,2,2,3,3-heptafluoropropane (HFC-227ca), 1,1,1,2,3,3,3-heptafluoropropane (HFC-227ea), 1,1,1,3,3,3-hexafluoropropane (HFC-236fa), 1,1,1,2,3,3-hexafluoropropane (HFC-236ea), HFC-32, trifluoromethane (HFC-23), fluoromethane (HFC-41), carbon monoxide, carbon dioxide and water. In the above description, E/Z means a mixture of E-form and Z-form.

<Step (II)>

In the step (II), hydrogen fluoride in the reaction product gas (1) obtained in the step (I) is removed.

The reaction product gas (1) obtained in the step (I) may be used in the step (II) as it is. Otherwise, another treatment step may be conducted between the step (I) and the step (II), to apply another treatment to the reaction product gas (1), and the reaction product gas (1) after such a treatment may be used in the step (II). Here, such another treatment may be a treatment other than removal of hydrogen fluoride and is a treatment which does not change the composition other than moisture in the reaction product gas (1). Such another treatment may, for example, be storage in a tank, compression by a compressor, heating, cooling or removal of moisture.

(Removal of Hydrogen Fluoride)

As a method of removing hydrogen fluoride from the reaction product gas (1), distillation, adsorption, two-phase separation or washing may, for example, be mentioned.

Distillation is a method of distilling the reaction product gas (1) to remove hydrogen fluoride. Distillation may be conducted under normal pressure, under elevated pressure or under reduced pressure, and is preferably conducted under elevated pressure with a view to improving the separation efficiency.

Adsorption is a method of bringing the reaction product gas (1) into contact with an adsorbent to let hydrogen fluoride be adsorbed on the adsorbent and removed. The adsorbent may be in a solid phase or may be dispersed in a liquid medium in which the adsorbent is not soluble (liquid phase). The adsorbent may, for example, be sodium fluoride, potassium fluoride, zeolite or activated carbon. Particularly preferred is sodium fluoride, with which hydrogen fluoride can be efficiently removed.

Two phase separation is a method of separating the reaction product gas (1) into two phases of an organic phase containing HFO-1123 and HFC-134a and an acid phase containing hydrogen fluoride, under elevated pressure in a liquid phase, and removing the separated acid phase.

Washing is a method of bringing the reaction product gas (1) into contact with an aqueous solution to remove hydrogen fluoride. Preferred is use of an alkaline aqueous solution, with which the efficiency to remove hydrogen fluoride is high. Further, the alkaline aqueous solution is preferably an aqueous potassium hydroxide solution, an aqueous potassium carbonate solution or an aqueous potassium bicarbonate solution, with which a hardly-soluble salt is less likely to form. The concentration of the alkaline aqueous solution is preferably from 5 to 40 mass %. When the concentration of the alkaline aqueous solution is at least the lower limit, hydrogen fluoride will be efficiently removed, and when it is at most the upper limit, a salt is less likely to precipitate and as a result, the piping will hardly be clogged. Here, by the washing method using an alkaline aqueous solution, in addition to hydrogen fluoride, acidic components such as hydrogen chloride and carbon dioxide contained in the reaction product gas (1) are removed.

(Reaction Product Gas Obtained in Step (II))

By removal of hydrogen fluoride in the step (II), from the reaction product gas (1), a reaction product gas in which at least the content of hydrogen fluoride is reduced (hereinafter referred to as gas to be treated (2)) is obtained. That is, by the step (II), a gas to be treated (2) which is a gas mixture containing HFO-1123 and unreacted HFC-134a, and the diluent gas, the by-product compounds and the like, in which the content of hydrogen fluoride is reduced as compared with the reaction product gas (1), is obtained. In the gas to be treated (2) obtained in the step (II), not only the hydrogen fluoride content, but also contents of acidic components such as hydrogen chloride and carbon dioxide, and contents of compounds other than the acidic components among the above other compounds, may be reduced as compared with the reaction product gas (1).

The gas to be treated (2) obtained in the step (II) may be introduced to the step (III) as it is. Otherwise, another treatment may be conducted between the step (II) and the step (III) to apply another treatment to the gas to be treated (2), and the gas (2) to be treated after such another treatment may be introduced to the step (III). Here, such another treatment is a treatment other than removal of hydrogen fluoride and is a treatment which does not change the composition other than moisture in the gas to be treated (2). Such another treatment may, for example, be storage in a tank, compression by a compressor, heating, cooling or removal of moisture. With a view to improving the degree of conversion in the step (III), it is preferred to provide a step of moisture removal between the step (II) and the step (III). The method of moisture removal may, for example, be a method of adsorption by an adsorbent such as zeolite or alumina.

<Step (III)>

In the step (III), the gas to be treated (2) obtained in the step (II) or a gas to be treated obtained by applying the above another treatment to the gas (2) to be treated (hereinafter generally be referred to as the gas to be treated (2)) is brought into contact with the catalyst (2) to convert HFC-134a in the gas to be treated (2) to HFO-1123.

The catalyst (2) used in the step (III) is one having catalytic action on dehydrofluorination of HFC-134a. As the catalyst (2), the same catalysts exemplified as the catalyst (1) used in the step (I) may be mentioned. As mentioned above, the catalyst (2) used in the step (III) may be of the same type as or different type from the catalyst (1) used in the step (I). Further, the catalyst (2) used in the step (III) and the catalyst (1) used in the step (I) may be exactly the same catalyst.

The activation treatment method and the reactivation treatment method for the catalyst (2) used in the step (III) are the same as those for the catalyst (1) used in the step (I).

(Contact of Gas to be Treated (2) and Catalyst (2))

When the gas to be treated (2) and the catalyst (2) and brought into contact with each other, the catalyst (2) in a solid state (solid phase) may be brought into contact with the gas to be treated (2), or the catalyst (2) in a state dispersed in a liquid medium in which the catalyst (2) can be dispersed (liquid phase) may be brought into contact with the gas to be treated (2), in the same manner as the catalyst (1) in the step (I). The catalyst (2) is preferably in a solid phase.

Now, the step (III) will be described also with reference to an embodiment in which the gas to be treated (2) continuously supplied to the reactor is brought into contact with the catalyst (2) in a solid phase charged to the reactor by the batch, however, the step (III) in the production process of the present invention is not limited to such an embodiment.

(Reactor and Reaction Conditions)

The reactor in which the gas to be treated (2) and the catalyst (2) are brought into contact and reacted with each other (hereinafter sometimes referred to as a second reactor) in the step (III) may be a reactor having the same shape and structure as the first reactor in which the material gas and the catalyst (1) are brought into contact and reacted with each other in the step (I). The second reactor may have a heating means such as an electric heater to heat the interior of the reactor.

The catalyst (2) may be accommodated in the form of either a fixed bed or a fluidized bed, in the second reactor. In the case of a fixed bed, it may be either a horizontal fixed bed or a vertical fixed bed, and is preferably a vertical fixed bed.

The gas to be treated (2) obtained in the step (II) may be introduced to the second reactor at room temperature as it is, however, it is preferably heated (preheated) and then introduced to the second reactor, so as to increase the reactivity in the second reactor. In a case where it is preheated, the gas to be treated (2) is preferably heated to a temperature of from 80 to 150° C. and then supplied to the second reactor.

The gas to be treated (2) introduced to the second reactor is brought into contact with the catalyst (2) in a solid phase in the second reactor. The temperature in the second reactor is preferably from 50 to 500° C., more preferably from 200 to 500° C., particularly preferably from 300 to 450° C. with a view to improving the reactivity and the life of the catalyst. The pressure in the second reactor is preferably from 0 to 2 MPa by the gauge pressure. The contact time of the gas to be treated (2) and the catalyst (2) in the second reactor is preferably from 0.1 to 500 seconds, more preferably from 0.5 to 50 seconds, particularly preferably from 5 to 30 seconds.

(Reaction Product Gas Obtained in Step (III))

In the step (III), as the outlet gas from the second reactor, a reaction product gas containing HFO-1123 (hereinafter referred to as reaction product gas (3)) is obtained. The reaction product gas (3) may contain the diluent gas in a case where the material gas contains the diluent gas, and usually further contains unreacted HFC-134a and by-product compounds formed in the steps (I) to (III). As a newly formed by-product compound contained in the reaction product gas (3), the same compounds as compounds disclosed as the by-product compounds in the reaction product gas (1) may be mentioned.

The content of HFO-1123 in the reaction product gas (3) is higher than the content of HFO-1123 in the reaction product gas (1).

The reaction product gas (3) may be used as it is for various applications, but is preferably used after purification to increase the content of HFO-1123 as a desired compound. The purification method may, for example, be a known method such as distillation, adsorption or washing with an acidic aqueous solution, a basic aqueous solution or a neutral aqueous solution. The components other than HFO-1123 contained in the reaction product gas (3) may be separated and removed to a desired extent by the above means. Among the above purification methods, preferred is distillation under normal pressure, elevated pressure or reduced pressure, and by distillation under such a pressure, high purity HFO-1123 can be obtained. Further, HFC-134a separated from the reaction product gas (3) may be recycled as a part of the material gas.

The reaction product gas (3) may not contain unreacted HFC-134a, however, in the present invention, the reaction product gas (3) usually contains unreacted HFC-134a relatively in a large amount, since the degree of conversion of HFC-134a from the material gas to the reaction product gas (3) is usually from 3 to 25 mol %. Accordingly, hydrogen fluoride may be removed from the reaction product gas (3), and the gas to be treated from which hydrogen fluoride has been removed may be brought into contact with the same dehydrofluorination catalyst as the catalyst (1) to convert at least part of HFC-134a in the gas to be treated into HFO-1123.

In the present invention, such removal of hydrogen fluoride and conversion of HFC-134a to HFO-1123 are repeated to increase the proportion of HFO-1123 in the reaction product gas. In other words, in the production process of the present invention, after the above steps (I) to (III), a combination of further conducting the same hydrogen fluoride removal step as in the step (II) and then conducting the same step of reacting HFC-134a as in the step (III) may be repeated at least once.

However, if the proportion of HFO-1123 in the reaction product gas is high, as mentioned above, a reverse reaction of the reaction to form HFO-1123 may occur in the equilibrium reaction represented by the reaction formula (1). Accordingly, the number of repetition of the combination of the hydrogen fluoride removal step and the step of reacting HFC-134a is preferably to such an extent that an increase in the degree of conversion of HFC-134a is confirmed.

<Reaction Apparatus>

An example of a reaction apparatus used in production of HFO-1123 in the present invention is shown in FIG. 1. A reaction apparatus 1 shown in FIG. 1 comprises a first stage reactor 2 provided with a heating means such as an electric heater to conduct the step (I), an alkaline aqueous solution trap 3 to conduct the step (II) and a second stage reactor 4 provided with a heating means such as an electric heater to conduct the step (III). In the first stage reactor 2 and the second stage reactor 4, a heating means is not essential.

In the first stage reactor 2, a catalyst 5 is accommodated to form a vertical fixed bed. Further, to the upper portion on the inlet side of the first stage reactor 2, a first stage preheating mixer 6 provided with a heating means such as an electric heater is connected via a material gas supply line 7. The material gas supply line 7 is preferably also provided with a heating means such as an electric heater.

To the first stage preheating mixer 6, a HFC-134a supply line 8 to supply HFC-134a and a diluent gas supply line 9 to supply a diluent gas are connected. HFC-134a and a diluent gas are supplied to the first stage preheating mixer 6 respectively from the HFC-134a supply line 8 and the diluent gas supply line 9, mixed in the first stage preheating mixer 6 and heated to a predetermined temperature, and the mixture is supplied to the first stage reactor 2 through the material gas supply line 7.

Further, the HFC-134a supply line 8 and the diluent gas supply line 9 may be combined before the first stage preheating mixer 6, so that HFC-134a and the diluent gas are mixed and the mixture is supplied to the first stage preheating mixer 6. Further, at least one of the HFC-134a supply line 8 and the diluent gas supply line 9 may be provided with a preheater provided with e.g. an electric heater, so that at least one of HFC-134a and the diluent gas supplied through the line is heated and then introduced to the first stage preheating mixer 6.

To the lower portion on the outlet side of the first stage reactor 2, the alkaline aqueous solution trap 3 is connected via a first stage reactor outlet line 10 provided with a heating means such as an electric heater. To the outlet of the alkaline aqueous solution trap 3, a dehydration apparatus 11 is connected, and the dehydration apparatus 11 is connected to a second stage preheating mixer 13 provided with the heating means such as an electric heater. The second stage preheating mixer 13 is connected to the second stage reactor 4 via an intermediate material gas supply line 14. From the gas discharged from the outlet of the first stage reactor, acid components such as hydrogen fluoride are removed by the alkaline aqueous solution trap 3 and then moisture is removed by the dehydration apparatus 11, and then the gas is introduced to the second stage preheating mixer 13. The gas is heated to a predetermined temperature in the second stage preheating mixer 13, and then supplied to the second stage reactor 4 through the intermediate material gas supply line 14.

In the second stage reactor 4, a catalyst 12 is accommodated to form a vertical fixed bed. To the lower portion on the outlet side of the second stage reactor 4, a second stage reactor outlet line 15 provided with a heating means such as an electric heater is connected, and the second stage reactor outlet line 15 is connected to a hydrogen fluoride trapping tube 16 packed with a solid substance to trap hydrogen fluoride. And, from the gas discharged from the outlet of the second stage reactor 4, hydrogen fluoride is removed by the hydrogen fluoride trapping tube 16, and then the gas is collected into a sampling bag 17, and its components are analyzed by an analyzer such as a gas chromatograph (GC) and determined.

According to the production process of the present invention, the degree of conversion of 134a and the selectivity for HFO-1123 are sufficiently high without using a large amount of the diluent gas. Further, the content of HFO-1123 in the obtained reaction product gas can be increased, whereby the productivity of HFO-1123 can be increased.

HFO-1123 obtained by the production process of the present invention is useful as a refrigerant which replaces HFC-32 and HFC-125 which are greenhouse gases, and as a material monomer and a synthetic intermediate of a functional material such as a piezoelectric element or a film.

EXAMPLES

Now, the present invention will be described in further detail with reference to Examples. However, it should be understood that the present invention is by no means restricted to such specific Examples.

<Reaction Apparatus>

Figure 2:
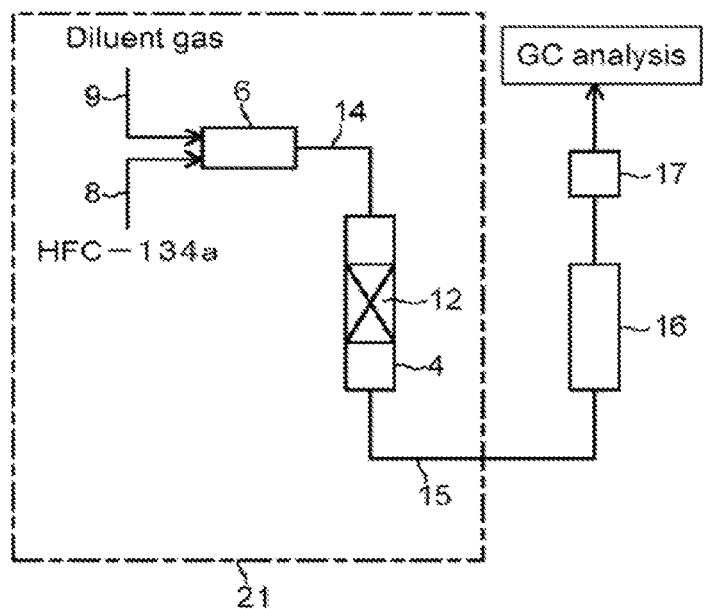
FIG. 2 is a diagram illustrating a reaction apparatus used in Comparative Examples 3 to 6.

In Examples 1 to 8 and Comparative Examples 1 and 2, a reaction apparatus shown in FIG. 1 (hereinafter referred to as a reaction apparatus (1)) was used. Further, in Comparative Examples 3 to 6, a reaction apparatus shown in FIG. 2 (hereinafter referred to as a reaction apparatus (2)) was used.

(Reaction Spparatus (1))

In the reaction apparatus 1, as a first stage reactor 2 and a second stage reactor 4, vertical fixed bed reactors having an inner diameter of 15.75 mm and a height of 400 mm made of Inconel 600 (tradename by Special Metals) were used. The first stage reactor 2 and the second stage reactor 4 were packed with catalysts as identified in Examples and Comparative Examples to a height of 100 mm. The interiors of such reactors were separately heated by electric furnaces.

A material gas supply line 7 connected to the upper portion on the inlet side of the first stage reactor 2 and a first stage preheating mixer 6 were respectively heated to 100° C. by a ribbon heater. The apparatus was so constituted that HFC-134a and nitrogen as a diluent gas were mixed while their flow rates were adjusted respectively by mass flow controllers (not shown) provided to a HFC-134a supply line 8 and a diluent gas supply line 9, and the gas mixture was supplied to the first stage preheating mixer 6.

To the lower portion on the outlet side of the first stage reactor 2, a first stage reactor outlet line 10 provided with an electric heater was connected, and ahead of this line, a 10 mass % potassium hydroxide aqueous solution bath as an alkaline aqueous solution trap 3 and a dehydration apparatus 11 packed with 70 g of molecular sieves 3A in the form of pellets (sold by JUNSEI CHEMICAL CO., LTD., ⅛ inch pellets) were connected in this order. And a second stage preheating mixer 13 connected to the outlet side of the dehydration apparatus 11 and an intermediate material gas supply line 14 to connect the second stage preheating mixer 13 and the second stage reactor 4 were respectively heated to 100° C. by a ribbon heater.

Further, a branch line was provided ahead of the dehydration apparatus 11 although it is not shown, so that the gas was collected by a sampling bag made of polyvinylidene fluoride (PVdF) and the gas composition was analyzed by GC.

A second stage reactor outlet line 15 connected to the lower portion on the outlet side of the second stage reactor 4 was heated to 100° C. by a ribbon heater, and ahead of this line, a hydrogen fluoride trapping tube 16 packed with 28 g of 1/16 inch sodium fluoride pellets was connected. Ahead of the hydrogen fluoride trapping tube 16, a sampling bag 17 made of PVdF was connected, so that gas collection and gas composition analysis were carried out by GC.

(Reaction Apparatus (2))

In the reaction apparatus (2), only a first stage reactor was provided. That is, in a reaction apparatus 21 shown in FIG. 2 was constituted of a HFC-134a supply line 6, a diluent gas supply line 7, a first stage preheating mixer 6, a material gas supply line 7 and a first stage reactor 2 in the same manner as the reaction apparatus 1 shown in FIG. 1. Further, a first stage reactor outlet line 10 connected to the lower portion of the first stage reactor 2 was connected to a sampling bag 17 via a hydrogen fluoride trapping tube 16 packed with 28 g of sodium fluoride pellets. Further, an outlet gas from the first stage reactor 2 was continuously taken out, made to pass through the hydrogen fluoride trapping tube 16 and collected in the sampling bag 17, and subjected to composition analysis by GC.

<Analysis Conditions>
To analyze the composition of the outlet gas, gas chromatograph (GC) was employed. As a column, DB-1 (manufactured by Agilent Technologies, length: 60 mm×inner diameter: 250 μm×thickness: 1 μm) was used. As a detector, FID was employed.

<Linear Velocity>
The linear velocity means a superficial velocity, and was calculated, assuming that the reactor through which the gas flowed was a void tower having no content in the interior thereof, by dividing the flow rate (volume flow rate) by the cross section area of the reactor which was a void tower.

Linear velocity (superficial velocity)(cm/s)=flow rate (cm$^3$/s)/cross section area (cm$^2$)

Preparation Example 1 (Preparation of Chromia Catalyst)

1,100 g of Cr(NO$_3$)$_3$.9H$_2$O and 150 g of Mg(NO$_3$)$_2$.6H$_2$O were dissolved in 2.5 liter of water, and 2,000 g of a 28 mass % aqueous ammonium hydroxide solution was added. The mixture was added to 4 liter of water heated to 70° C. with stirring, to precipitate a hydroxide, and the precipitate was collected by filtration. The obtained precipitate was washed with pure water and fired at 420° C. for 5 hours to obtain an oxide powder. The obtained oxide powder was formed into a cylinder with a diameter of 5 mm and a height of 5 mm by a tablet making machine to prepare a chromia catalyst.

Example 1

The first stage reactor and the second stage reactor of the reaction apparatus (1) were respectively packed with 15 g of an alumina catalyst (manufactured by Catalysts & Chemicals Industries, Co., Ltd., tradename: ACBM-1, shape: spheres having a particle size of 2 mm), heated and dried at 300° C. for 5 hours while a nitrogen gas was supplied at 300 sccm.

Then, the internal temperatures in the first stage reactor and the second stage reactor were adjusted to 350° C., and a material gas obtained by mixing HFC-134a at a flow rate of 1.21 mmol/min and nitrogen at a flow rate of 1.21 mmol/min, was supplied to the first stage reactor. HFC-134a and nitrogen were continuously made to flow, and 7 hours later, the composition of the outlet gas from the second stage reactor (hereinafter referred to simply as an outlet gas) was confirmed to be stabilized, and the reaction was completed. The composition of the outlet gas 7 hours later was analyzed by GC.

Then, based on the mole fractions (mol %) of the respective components in the outlet gas obtained by GC analysis and the mole fractions (mol %) of HFC-134a and nitrogen in the material gas supplied to the first stage reactor, the degree of conversion (reaction rate) of HFC-134a, the selectivity for HFO-1123 and the rate of presence (mol %) of HFO-1123 in the outlet gas were obtained as follows.

In the following reaction formulae, (HFC-134a)$_{I\,N}$ represents the mole fraction (mol %) of HFC-134a in the inlet gas excluding the nitrogen gas, (HFC-134a)$_{o\,u\,t}$ and (HFO-1123)$_{o\,u\,t}$ respectively represent the mole fractions (mol %) of HFC-134a and HFO-1123 in the outlet gas excluding the nitrogen gas. Further, (N$_2$)$_{I\,N}$ represents the mole fraction (mol %) of the nitrogen gas in the material gas including the nitrogen gas.

The mole fraction of each component in the outlet gas was calculated by multiplying the area ratio (excluding nitrogen which was not detectable) of each component identified by GC, by a detection sensitivity factor measured by using a standard substance having a known composition ratio. Further, the mole fractions of HFC-134a and nitrogen in the material gas were calculated by the flow rate ratio of HFC-134a and nitrogen.

[Degree of Conversion of HFC-134a (mol %)]
The degree of conversion of HFC-134a means a proportion of HFC-134a which had been converted into other components including HFO-1123 and consumed by the reaction. Here, the reaction means the entire reaction including the reaction in the first stage reactor and the reaction in the second stage reactor. The degree of conversion of HFC-134a is calculated by the following formula:

Degree of conversion of HFC-134a (mol %)={1−(HFC-134a)$_{o\,u\,t}$/(HFC-134a)$_{I\,N}$}×100

[Selectivity for HFO-1123 (mol %)]
The selectivity for HFO-1123 means the proportion of HFC-134a which had been converted into HFO-1123 based on the reacted HFC-134a. The selectivity for HFO-1123 is calculated by the following formula:

Selectivity for HFO-1123 (mol %)=(HFO-1123)$_{o\,u\,t}$/{1−(HFC-134a)$_{o\,u\,t}$/(HFC-134a)$_{I\,N}$}×100

[Rate of Presence of HFO-1123 in Outlet Gas (mol %)]
The rate of presence of HFO-1123 in the outlet gas means the proportion of HFO-1123 present in the outlet gas including nitrogen and is calculated by the following formula:

Rate of presence of HFO-1123 (mol %)=(HFO-1123)$_{o\,u\,t}$×{1−(N$_2$)$_{I\,N}$/100}

Such calculation results are shown in Table 1 together with the reaction conditions (the type of the reaction apparatus, the HFC-134a flow rate, the nitrogen flow rate and the molar ratio (HFC-134a:nitrogen) supplied to the first stage reactor, the reactor internal temperature, the linear velocity and the total contact time).

The reactor internal temperature is the internal temperature in the first stage reactor and the second stage reactor and is a measured value. Further, the linear velocity is the linear velocity of the material gas supplied to the first stage reactor. Further, the total contact time is the sum of the contact times with the catalyst in the first stage reactor and the second stage reactor.

Examples 2 to 4 and Comparative Examples 1 and 2

Using the reaction apparatus (1), in the same manner as in Example 1 except that some of the reaction conditions were changed as identified in Table 1, the reaction was continuously carried out. The composition of the outlet gas was analyzed by GC 7 hours later in Examples 2 and 3 and Comparative Example 2, 20 hours later in Example 4, and 14 hours later in Comparative Example 1, and the degree of conversion (reaction rate) of HFC-134a, the selectivity for HFO-1123 and the rate of presence of HFO-1123 in the outlet gas were obtained in the same manner as in Example 1. The obtained results are shown in Table 1.

Comparative Example 3

The first stage reactor of the reaction apparatus (2) was packed with 15 g of an alumina catalyst (manufactured by Catalysts & Chemicals Industries, Co., Ltd., tradename: ACBM-1, shape: spheres having a particle size of 2 mm), and heated and dried at 300° C. for 5 hours while a nitrogen gas was supplied at 300 sccm.

Then, the temperature of the first stage reactor was adjusted to 350° C., and a material gas obtained by mixing HFC-134a at a flow rate of 1.21 mmol/min and nitrogen at a rate of 1.21 mmol/min was supplied to the first stage reactor. HFC-134a and nitrogen were continuously made to flow, and 7 hours later, the composition of the outlet gas was confirmed to be stabilized, and the reaction was completed. The composition of the outlet gas 7 hours later was analyzed by GC, and the degree of conversion (reaction rate) of HFC-134a, the selectivity for HFO-1123 and the rate of presence of HFO-1123 in the outlet gas were obtained in the same manner as in Example 1. The obtained results are shown in Table 1.

Comparative Example 4

Using the reaction apparatus (2), the reaction was carried out in the same manner as in Comparative Example 3 under the reaction conditions as identified in Table 1. The composition of the outlet gas 7 hours later was analyzed by GC, and the degree of conversion (reaction rate) of HFC-134a, the selectivity for HFO-1123 and the rate of presence of HFO-1123 in the outlet gas were obtained in the same manner as in Example 1. The obtained results are shown in Table 1.

hours later was analyzed by GC, and the degree of conversion of HFC-134a, the selectivity for HFO-1123 and the rate of presence of HFO-1123 in the outlet gas were obtained in the same manner as in Example 1. The obtained results are shown in Table 2 together with the reaction conditions.

Example 6

Using the reaction apparatus (1), the reaction was continuously carried out in the same manner as in Example 5 under the reaction conditions as identified in Table 2. The composition of the outlet gas 7 hours later was analyzed by GC, and the degree of conversion of HFC-134a, the selectivity for HFO-1123 and the rate of presence of HFO-1123 in the outlet gas were obtained in the same manner as in Example 1. The obtained results are shown in Table 2.

Comparative Example 5

The first stage reactor of the reaction apparatus (1) was packed with 17 g of an aluminum trifluoride catalyst (manu-

TABLE 1

| | | Reaction conditions | | | | | | |
|---|---|---|---|---|---|---|---|---|
| | | | Flow rate | | HFC-134a/nitrogen molar ratio | | Reactor internal | Linear | Total contact |
| | Catalyst | Reaction apparatus | HFC-134a mmol/min | nitrogen mmol/min | HFC-134a mol % | nitrogen mol % | temperature ° C. | velocity cm/sec | time sec |
| Ex. 1 | Alumina | (1) | 1.21 | 1.21 | 50 | 50 | 350 | 1.0 | 20 |
| Ex. 2 | Alumina | (1) | 2.41 | 2.41 | 50 | 50 | 350 | 2.0 | 10 |
| Ex. 3 | Alumina | (1) | 2.41 | 0.00 | 100 | 0 | 350 | 1.0 | 20 |
| Ex. 4 | Alumina | (1) | 4.83 | 0.00 | 100 | 0 | 350 | 2.0 | 10 |
| Comp. Ex. 1 | Alumina | (1) | 0.97 | 3.86 | 20 | 80 | 350 | 2.0 | 10 |
| Comp. Ex. 2 | Alumina | (1) | 0.48 | 1.93 | 20 | 80 | 350 | 1.0 | 20 |
| Comp. Ex. 3 | Alumina | (2) | 1.21 | 1.21 | 50 | 50 | 350 | 1.0 | 10 |
| Comp. Ex. 4 | Alumina | (2) | 2.41 | 0.00 | 100 | 0 | 350 | 1.0 | 10 |

| | Reaction results | | |
|---|---|---|---|
| | Degree of conversion of HFC-134a mol % | Selectivity for HFO-1123 mol % | Rate of presence of HFO-1123 in outlet gas mol % |
| Ex. 1 | 6.3 | 97.0 | 3.0 |
| Ex. 2 | 6.5 | 96.5 | 3.1 |
| Ex. 3 | 4.3 | 96.6 | 4.2 |
| Ex. 4 | 3.2 | 97.4 | 3.1 |
| Comp. Ex. 1 | 9.7 | 96.6 | 1.9 |
| Comp. Ex. 2 | 10.0 | 94.0 | 1.9 |
| Comp. Ex. 3 | 4.3 | 97.2 | 2.1 |
| Comp. Ex. 4 | 2.8 | 96.4 | 2.7 |

Example 5

The first stage reactor and the second stage reactor of the reaction apparatus (1) were respectively packed with 17 g of an aluminum trifluoride catalyst (manufactured by KANTO CHEMICAL CO., LTD., special grade reagent, shape: powdery) and heated and dried at 300° C. for 7 hours while a nitrogen gas was supplied at 300 sccm.

Then, the internal temperatures of the first stage reactor and the second stage reactor were respectively adjusted to 400° C., and HFC-134a was supplied to the first stage reactor at a flow rate of 2.24 mmol/min. HFC-134a was continuously made to flow, and 7 hours later, the composition of the outlet gas was confirmed to be stabilized, and the reaction was completed. The composition of the outlet gas 7 factured by KANTO CHEMICAL CO., LTD., special grade reagent, shape: powdery) and heated and dried at 300° C. for 7 hours while a nitrogen gas was supplied at 300 sccm.

Then, the internal temperature of the first stage reactor was adjusted to 400° C., and HFC-134a was supplied to the reactor at a flow rate of 2.24 mmol/min. HFC-134a was continuously made to flow, and 7 hours later, the composition of the outlet gas was confirmed to be stabilized, and the reaction was completed. The composition of the outlet gas 7 hours later was analyzed by GC, and the degree of conversion of HFC-134a, the selectivity for HFO-1123 and the rate of presence of HFO-1123 in the outlet gas were obtained in the same manner as in Examples. The obtained results are shown in Table 2.

TABLE 2

| | | | Reaction conditions | | | | | | |
|---|---|---|---|---|---|---|---|---|---|
| | | | Flow rate | | HFC-134a/nitrogen molar ratio | | Reactor internal | Linear | Total contact |
| | Catalyst | Reaction apparatus | HFC-134a mmol/min | nitrogen mmol/min | HFC-134a mol % | nitrogen mol % | temperature °C. | velocity cm/sec | time sec |
| Ex. 5 | Aluminum trifluoride | (1) | 2.24 | 0.00 | 100 | 0 | 400 | 1.0 | 20 |
| Ex. 6 | Aluminum trifluoride | (1) | 4.47 | 0.00 | 100 | 0 | 400 | 2.0 | 10 |
| Comp. Ex. 5 | Aluminum trifluoride | (2) | 2.24 | 0.00 | 100 | 0 | 400 | 1.0 | 10 |

| | Reaction results | | |
|---|---|---|---|
| | Degree of conversion of HFC-134a mol % | Selectivity for HFO-1123 mol % | Rate of presence of HFO-1123 in outlet gas mol % |
| Ex. 5 | 6.8 | 99.4 | 6.8 |
| Ex. 6 | 5.6 | 98.9 | 5.5 |
| Comp. Ex. 5 | 4.5 | 99.2 | 4.5 |

Example 7

The first stage reactor and the second stage reactor of the reaction apparatus (1) were respectively packed with 22 g of the chromia catalyst obtained in Preparation Example 1 and 29 g of a chromia catalyst obtained in the same manner as in Preparation Example 1, and dried at 300° C. while a nitrogen gas was supplied at 300 sccm. The first stage reactor was dried for 6 hours, and the second stage reactor was dried for 7 hours.

Then, the internal temperatures of the first stage reactor and the second stage reactor were respectively adjusted to 400° C., and HFC-134a was supplied to the first stage reactor at a flow rate of 4.47 mmol/min. HFC-134a was continuously made to flow, and 20 hours later, the composition of the outlet gas was confirmed to be stabilized, and the reaction was completed. The composition of the outlet gas 20 hours later was analyzed by GC, and the degree of conversion of HFC-134a, the selectivity for HFO-1123 and the rate of presence of HFO-1123 in the outlet gas were obtained in the same manner as in Examples. The obtained results are shown in Table 3 together with the reaction conditions.

Example 8

Using the reaction apparatus (1), the reaction was continuously carried out in the same manner as in Example 7 under the reaction conditions as identified in Table 3. The composition of the outlet gas 7 hours later was analyzed by GC, and the degree of conversion of HFC-134a, the selectivity for HFO-1123 and the rate of presence of HFO-1123 in the outlet gas were obtained in the same manner as in Example 1. The obtained results are shown in Table 3.

Comparative Example 6

The first stage reactor of the reaction apparatus (2) was packed with 17 g of a chromia catalyst obtained in Preparation Example 1 and heated and dried at 300° C. for 6 hours while a nitrogen gas was supplied at 300 sccm.

Then, the internal temperature of the first stage reactor was adjusted to 400° C., and HFC-134a was supplied to the reactor at a flow rate of 2.24 mmol/min. HFC-134a was continuously made to flow, and 7 hours later, the composition of the outlet gas was confirmed to be stabilized, and the reaction was completed. The composition of the outlet gas 7 hours later was analyzed by GC, and the degree of conversion of HFC-134a, the selectivity for HFO-1123 and the rate of presence of HFO-1123 in the outlet gas were obtained in the same manner as in Example 1. The obtained results are shown in Table 3 together with the reaction conditions.

TABLE 3

| | | | Reaction conditions | | | | | | |
|---|---|---|---|---|---|---|---|---|---|
| | | | Flow rate | | HFC-134a/nitrogen molar ratio | | Reactor internal | Linear | Total contact |
| | Catalyst | Reaction apparatus | HFC-134a mmol/min | nitrogen mmol/min | HFC-134a mol % | nitrogen mol % | temperature °C. | velocity cm/sec | time sec |
| Ex. 7 | Chromia | (1) | 4.47 | 0.00 | 100 | 0 | 400 | 2.0 | 10 |
| Ex. 8 | Chromia | (1) | 2.24 | 0.00 | 100 | 0 | 400 | 1.0 | 20 |
| Comp. Ex. 6 | Chromia | (2) | 2.24 | 0.00 | 100 | 0 | 400 | 1.0 | 10 |

TABLE 3-continued

| | Reaction results | | |
|---|---|---|---|
| | Degree of conversion of HFC-134a mol % | Selectivity for HFO-1123 mol % | Rate of presence of HFO-1123 in outlet gas mol % |
| Ex. 7 | 4.7 | 96.5 | 4.5 |
| Ex. 8 | 4.7 | 91.9 | 4.3 |
| Comp. Ex. 6 | 3.8 | 95.2 | 3.6 |

It is found from Tables 1, 2 and 3 that in Examples 1 to 8 in which the reaction apparatus (1) was used, a material gas having a content of HFC-134a of at least 50 mol % was continuously supplied, the reaction of HFC-134a was carried out in two stages, and between the first stage reaction and the second stage reaction, hydrogen fluoride was removed by an aqueous potassium hydroxide solution, the rate of presence of HFO-1123 in the outlet gas was high as compared with Comparative Examples 3 to 6 in which the reaction of HFC-134a was carried out in one stage using the reaction apparatus (2).

Further, in Comparative Examples 1 and 2, the reaction of HFC-134a was carried out in two stages using the reaction apparatus (1), however, since a material gas having a content of HFC-134a of less than 50 mol % was supplied to the first stage reactor, the rate of presence of HFO-1123 in the outlet gas was low as compared with Examples.

INDUSTRIAL APPLICABILITY

According to the production process of the present invention, HFO-1123 can be efficiently and stably produced from HFC-134a. Further, the production process is useful as an industrial production process since HFC-134a which is an inexpensive material is used.

This application is a continuation of PCT Application No. PCT/JP2015/059140, filed on Mar. 25, 2015, which is based upon and claims the benefit of priority from Japanese Patent Application No. 2014-066058 filed on Mar. 27, 2014. The contents of those applications are incorporated herein by reference in their entireties.

REFERENCE SYMBOLS 1, 21: reaction apparatus, 2: first stage reactor, 3: alkaline aqueous solution trap, 4: second stage reactor, 5, 12: catalyst, 6: first stage preheating mixer, 7: material gas supply line, 8: HFC-134a supply line, 9: diluent gas supply line, 10: first stage reactor outlet line, 11: dehydration apparatus, 13: second stage preheating mixer, 14: intermediate material gas supply line, 15: second stage reactor outlet line, 16: hydrogen fluoride trapping tube, 17: sampling bag.

What is claimed is:

1. A process for producing trifluoroethylene, the process comprising:
bringing a 1,1,1,2-tetrafluoroethane gas or a 1,1,1,2-tetrafluoroethane gas diluted with a diluent gas, wherein a proportion of 1,1,1,2-tetrafluoroethane based on the total amount of the diluent gas and 1,1,1,2-tetrafluoroethane is at least 50 mol %, into contact with a first dehydrofluorination catalyst in a first reactor, thereby converting a part of 1,1,1,2-tetrafluoroethane into trifluoroethylene, and wherein moisture is formed as a by-product,
conducting a treatment other than removal of hydrogen fluoride that does not change components in the first reactor other than a content of moisture in a reaction product gas,
removing hydrogen fluoride from the obtained reaction product gas, and
bringing the reaction product gas from which hydrogen fluoride has been removed into contact with a second dehydrofluorination catalyst in a second reactor, thereby convening at least a part of 1,1,1,2-tetrafluoroethane into trifluoroethylene.

2. The process for producing trifluoroethylene according to claim 1, wherein a proportion of 1,1,1,2-tetrafluoroethane based on the total amount of 1,1,1,2-tetrafluoroethane and the diluent gas is at least 70 mol %.

3. The process for producing trifluoroethylene according to claim 1, wherein the diluent gas is a nitrogen gas.

4. The process for producing trifluoroethylene according to claim 1, wherein the first dehydrofluorination catalyst and the second dehydrofluorination catalyst are each independently at least one catalyst selected from the group consisting of a metal, a metal oxide and a metal halide.

5. The process for producing trifluoroethylene according to claim 1, wherein the first dehydrofluorination catalyst and the second dehydrofluorination catalyst are each independently a catalyst comprising at least one compound selected from the group consisting of aluminum oxide, aluminum trifluoride and chromium oxide.

6. The process for producing trifluoroethylene according to claim 1, wherein the first dehydrofluorination catalyst and the second dehydrofluorination catalyst are catalysts of exactly the same type.

7. The process for producing trifluoroethylene according to claim 1, wherein each of the contact temperature of 1,1,1,2-tetrafluoroethane and the first dehydrofluorination catalyst and the contact temperature of 1,1,1,2-tetrafluoroethane and the second dehydrofluorination catalyst is from 50 to 500° C.

8. The process for producing trifluoroethylene according to claim 7, wherein each of the contact temperatures is from 300 to 450° C.

9. The process for producing trifluoroethylene according to claim 1, wherein each of the contact time of 1,1,1,2-tetrafluoroethane and the first dehydrofluorination catalyst and the contact time of 1,1,1,2-tetrafluoroethane and the second dehydrofluorination catalyst is from 0.1 to 500 seconds.

10. The process for producing trifluoroethylene according to claim 9, wherein each of the contact times is from 5 to 30 seconds.

11. The process for producing trifluoroethylene according to claim 1, wherein hydrogen fluoride is removed by bringing the reaction product gas into contact with an alkaline aqueous solution.

12. The process for producing trifluoroethylene according to claim 1, wherein moisture is removed from the reaction product gas from which hydrogen fluoride has been removed, and then the reaction product gas from which moisture has been removed is brought into contact with the second dehydrofluorination catalyst.

13. The process for producing trifluoroethylene according to claim 1, wherein the treatment other than removal of hydrogen fluoride is selected from the group consisting of storage in a tank, compression by a compressor, heating, cooling, and removal of moisture.

\* \* \* \* \*